United States Patent [19]

Ritter

[11] Patent Number: 4,639,498

[45] Date of Patent: Jan. 27, 1987

[54] AEROBICALLY HARDENABLE PLASTIC COMPOSITIONS

[75] Inventor: Wolfgang Ritter, Düsseldorf, Fed. Rep. of Germany

[73] Assignee: Henkel Kommanditgesellschaft auf Aktien, Düesseldorf, Fed. Rep. of Germany

[21] Appl. No.: 739,484

[22] Filed: May 29, 1985

Related U.S. Application Data

[63] Continuation of Ser. No. 407,887, Aug. 13, 1982, abandoned.

[30] Foreign Application Priority Data

Jan. 21, 1982 [DE] Fed. Rep. of Germany ....... 3201731

[51] Int. Cl.[4] .................................... C08F 4/52
[52] U.S. Cl. .................................... 526/196; 525/251;
525/331.7; 525/331.9; 525/332.1; 525/332.2;
525/332.8; 525/332.9; 525/333.1; 525/333.2;
525/337; 525/389; 526/197; 526/201; 526/203
[58] Field of Search ............ 525/337, 251, 384, 331.7,
525/331.8, 332.1, 332.2, 332.8, 332.9, 333.1,
333.2; 526/196, 197, 201, 203

[56] References Cited

U.S. PATENT DOCUMENTS

| | | | |
|---|---|---|---|
| 3,066,170 | 11/1962 | Ramsden | 260/606.5 |
| 3,078,313 | 2/1963 | Brown | 260/606.5 |
| 3,084,180 | 4/1963 | D'Alelio | 260/448 |
| 3,084,181 | 4/1963 | D'Alelio | 260/448 |
| 3,119,878 | 1/1964 | Severini | 260/606.5 |
| 3,127,380 | 3/1964 | Welch | 526/196 |
| 3,127,383 | 3/1964 | Welch | 526/196 |
| 3,128,212 | 4/1964 | Larchar | 149/19 |
| 3,128,254 | 4/1964 | D'Alelio | 526/196 |
| 3,129,251 | 4/1964 | Rutkowski | 260/635 |
| 3,131,224 | 4/1964 | D'Alelio | 260/606.5 |
| 3,153,661 | 10/1964 | D'Alelio | 260/448 |
| 3,161,686 | 12/1964 | Brown | 260/606.5 |
| 3,293,277 | 12/1966 | Convery | 260/462 |
| 4,167,616 | 9/1979 | Bollinger | 526/197 |
| 4,381,386 | 4/1983 | Ritter et al. | 526/196 |
| 4,385,153 | 5/1983 | Ritter | 526/196 |

FOREIGN PATENT DOCUMENTS 874558 5/1959 United Kingdom ........................ 2/5

*Primary Examiner*—Joseph L. Schofer
*Assistant Examiner*—Bernard Lipman
*Attorney, Agent, or Firm*—Ernest G. Szoke; Henry E. Millson, Jr.; Mark A. Greenfield

[57] ABSTRACT

The aerobically hardenable compositions which comprise polymerizable systems containing components having some degree of ethylenic unsaturation and an oxygen-stable polymerization initiator of at least one organo-boron compound containing at least a major portion of boron to carbon bonds and possibly some boron to hydrogen bonds in the molecule and the boron containing radials are bound to an organic polymer matrix which is oxygen stable, the compositions being useful as casting resins, fillers and adhesives.

27 Claims, No Drawings

AEROBICALLY HARDENABLE PLASTIC COMPOSITIONS

This application is a continuation of application Ser. No. 407,887, filed Aug. 13, 1982, now abandoned.

The invention concerns aerobically hardenable plastic compositions that may be used, for example, as cast resins or fillers, but especially as reaction adhesives. These materials generally are in the form of multicomponent systems that can be stored and are mixed together or combined by some other method for the molding process, after which they harden upon exposure to air. As an example, reference is made to reaction adhesives that contain one component with ethylenically unsaturated monomers and a second component, the hardener, in which case the hardening occurs by radical polymerization following the combining of these components and exposing them to air. The invention is explained in the following text, using this type of multicomponent adhesive system, but it also applies analogously to other aerobically hardenable plastic compositions.

Adhesives that harden by the polymerization of compounds containing ethylene groups have been known for a long time. These can be prepared, for example, from methacrylic acid esters or other derivatives of acrylic acid or 2-substituted acrylic acids by the addition of peroxides or hydroperoxides and other agents. Usually the adhesive component consists of the solution of an elastomer in a monomer. When the hardening is to take place at room temperature or only moderately elevated temperatures, accelerators, which generally are aromatic amines or Schiff bases must be used to break down the peroxide.

For special areas of application, particularly for dental, medicinal or surgical use, binders and fillers are known that use trialkylboron compounds as the hardener component besides (meth)acrylic acid esters and other reactants containing ethylenic double bonds. This type of trialkylboron compound triggers the polymerization upon exposure to the air, at normal temperature, but the compositions have the disadvantage of being highly combustible, which makes the handling of these reaction compositions or adhesives very difficult. Attempts were made to eliminate this disadvantage by reacting the trialkylboron compounds with 0.3 to 0.9 mol oxygen. The trialkylboron compounds were also mixed with amines to lower their spontaneous combustibility. Although the ignition temperature is shifted into a range from 0° to 70° C. by these measures, there remains a considerable uncertainty in the handling of such mixtures. Besides, the reactivity of these derivatives is strongly decreased.

Upon exposure to an excess of oxygen, free boroalkyl compounds are oxidized to form boric acid esters and lose their polymerization initiating action. The use and particularly also the addition to a process of these known boroalkyl initiators, as well as during the production process, require the complete exclusion of oxygen. This means that the amount of substance needed must be packed under inert gas in absolutely airtight containers and the entering of oxygen into the storage container must be made impossible. The boroalkyl portions must be used quantitatively because of their hazardous reaction with air. Consequently, the systems described so far are unsuitable for general construction bonding, for example for the bonding of metal, wood, glass, ceramics and/or plastics. Even their use in the mentioned special areas is subject to considerable limitations.

OBJECTS OF THE INVENTION

It is an object of the invention to provide plastic compositions suitable for use as casting resins, fillers and reaction adhesives with novel organo-boron compounds as polymerization initiators.

A further object of the invention is to provide aerobically hardenable plastic compositions which comprise any polymerizable monomers, obligomers and polymers containing some degree of ethylenic unsaturation and as polymerization initiators organo-boron compounds which are in the form of polymer matrixes having substituent radicals selected from the group consisting of boron hydrides and organo-boron radicals, said polymerization initiators being stable in the presence of oxygen.

It is an object of the invention to provide a novel method of bonding two solid materials together.

These and other objects of the invention will become more apparent as the description thereof proceeds.

DESCRIPTION OF THE INVENTION

The present invention starts from the objective of creating aerobically hardenable plastic compositions which at room temperature are safe to handle, and have good material properties, for example good bonds and acceptable pot times even after exposure to oxygen. The invention is to create two-component systems that permit novel operating possibilities, for example in the field of fillers, cast resins and especially adhesives. In a more limited sense, the invention starts from the objective of using novel hardeners on the basis of organic boron compounds that react with ethylenically unsaturated reaction components that can be polymerized.

The invention thus concerns two-component adhesive systems, for example, which can be applied after mixing hardener and polymerizable component. But the so-called "no-mix adhesives" or "acrylate adhesives of the second or third generation" also are within the scope of the invention (cf. "Adhesives Age", No. 9, 1976, pp. 21–24 and "Adhesion", No. 3, 1981, pp. 156–161). The separate mixing of the adhesive component and the hardener component can be dispensed with in this case. In use, the initiator component is applied in a thin layer to one or both of the surfaces to be bonded. After a waiting period which may be up to several hours, the adhesive component is applied. The bond is completed by fixing the parts in the desired position.

The invention is especially intended to provide a new hardener component based on organo-boron compounds, which initiate a quick and easy to control polymerization by oxidation with atmospheric oxygen upon the addition to polymerizable monomers. In contrast to the known systems, the new organo-boron compounds shall themselves react very little or not at all with oxygen and shall under no circumstances ignite spontaneously. The invention also is intended to provide hardeners based on organo-boron compounds that are stable when stored at normal temperatures in air, but still initiate the polymerization spontaneously upon addition to the polymerizable monomer systems.

Accordingly, the subject of the invention in a first example are aerobically hardenable plastic materials such as cast resins, fillers and particularly reaction adhesives based on polymerizable systems containing ethylenic double bonds and organo-boron compounds as polymerization initiators, the characteristic of the invention being the presence of organic boron polymers as hardeners that have hydroboron and/or organo-boron radicals as substituents on a polymer matrix which are stable in air. These boron-containing radicals are preferably connected with B—C bonds to the polymer matrix. If these boron containing radicals are not the borane radical—$BH_2$ itself, these boron containing substituents of the polymer matrix are, in an also preferred example, themselves connected at the boron with at least one additional B—C bond to one or several organic radicals. The organo-boron initiators are described in my commonly assigned U.S. Patent application Ser. No. 407,887 filed on even date herewith now abandoned. Preferred radicals in this case are hydrocarbon radicals, which also may contain heteroatoms, especially O, N and/or S. Suitable substituents at the boron are especially alkyl, cycloalkyl and/or aryl radicals, which may be present on one or both of the boron valences not occupied by the polymer matrix. When such organic radicals that are different from hydrogen are present in both boron valences, they in turn may form a closed ring system. Thus the nub of the invention lies in the use of a new class of organic boron oligomers or polymers as polymerization initiators or as hardeners for polymerizable systems that contain ethylenic double bonds. The boron oligomers or polymers used according to the invention possess considerable advantages over conventional boroalkyl hardeners. They do not ignite spontaneously and have few storage requirements. The activity of these hardeners is preserved even when they are stored in the air for extended periods of time. The compatibility of the polymerizable component with the hardener is easily guaranteed in every case by the selection of a suitable structure for the polymer matrix. The amount of organo-boron oligomer or polymer needed for the hardening of the monomer component usually is extremely small.

The boron compounds used according to the invention as polymerization initiators can be obtained simply by hydroborating oligomers or polymers that contain carbon double bonds accessible for an addition reaction, and introducing the boron containing radicals in at least part of the double bonds suitable for addition. Suitable for hydroboration are diborane as well as monosubstituted or disubstituted boranes, i.e. compounds of the general formula $R_1R_2BH$, where $R_1$ is an organic radical, preferably a hydrocarbon radical, and $R_2$ is hydrogen or also an organic radical that may be identical with or different from $R_1$ or may also form a ring system together with $R_1$ and the boron.

Organo-boron polymers of the type used according to the invention were not previously described as such. Occasional references to their intermediate formation during the synthesis of certain polymers are found in the literature. Reference is made to "Makromol. Chem." 178:2837-2842, 1977, for example. The structural studies and synthesis of poly-(1-hydroxytetra-methylene) by hydroboration of 1,4-polybutadiene with 9-borabicyclo (3,3,1)-nonane (9-BBN) with oxidation immediately following and hydrolysis of the intermediately formed organo-boron polymer to the hydroxylated hydrocarbon polymer are described here. An isolation of the organic boron polymer formed as an intermediate in the solvent containing the reaction mixture did not take place. Consequently, no information was given about the properties of the polymers containing boron. The invention starts from the surprising observation that the fixation of the described boron containing radicals to an oligomeric or polymeric matrix, which is itself stable when exposed to atmospheric oxygen, results in a new type of organic boron compound that differs in its technical properties from the boroalkyl compounds described so far and also utilized in special cases. Particularly noteworthy is the relative stability of the organo-boron polymers or oligomers described according to the invention when in contact with atmospheric oxygen, which considerably facilitates their handling and use as polymerization initiators.

The polymer matrix, which has ethylenic double bonds that are available for hydroboration, may have a low viscosity and be fluid to solid, depending on its structure and molecular weight. Its mean molecular weight can reach values of several millions and generally lies in the range from about 150 to 3 millions. Lower values in this range are frequently preferred, for example those in the range from about 300 to 500,000 and especially those in the range from about 500 to 10,000. For some application purposes, for example in the area of reaction adhesives, the viscous fluidity or spreadability of the polymer matrix as well as of the organo-boron polymers prepared from it, at room temperature, can be desirable. Molecular weights in the range from about 300 to 3,000, for example, for the polymer matrix may be especially advantageous for this purpose. However, this is not a prerequisite for the effectiveness of the organo-boron polymers used according to the invention as polymerization initiators. On the contrary, the storage stability of corresponding solid organo-boron polymers at room temperature can be especially good.

The polymer matrix may have any desired degree of ethylenic unsaturation before the hydroboration. Preferred are respective materials with an iodine number in the range from about 1 to 500 before hydroboration. Particularly preferred within this range are iodine numbers from about 5 to 100 and especially from about 8 to 50.

The ethylenic double bonds accessible for hydroboration may be located in the main chain and/or in sidechain substituents in the starting polymer. In specific types of polymers, which shall be described below, double bonds for the hydroboration to form the polymerization initiator are usually located in side-chain substituents.

The polymer matrix may have a straight chain or branched chain structure before hydroboration, but polymer materials with cross-linked structure are acceptable. Whereas the formerly mentioned polymer types usually are reacted in solvents for the introduction of the boron containing groups, insoluble, cross-linked polymers still possessing reactive double bonds can be converted into the boron containing matrix, preferably after soaking the very fine powder in solvents. The conversion can be carried out, for example, in a suspension or dispersion of the powdered cross-linked matrix material in an inert solvent. Finally, the at least partial cross-linkage of oligomeric or polymeric matrix starting materials via the introduced boron and its several valences as part of the hydroboration, especially during the conversion with diborane, also lies within the scope of the invention.

Fundamentally all types of polymers are suitable as polymer matrix, provided that they have double bonds accessible for hydroboration but do not contain active groups that lead to undesirable side reactions during the introduction of the boron containing groups into the polymer material.

Within the scope of the invention it is also possible that the ethylenic double bonds are not the only ones that are hydroborated during the introduction of the boron containing radicals into the polymer matrix, and that part of the boron containing reagent also reacts with other functional groups of the polymer matrix. Such groups are, for example, keto groups, amide groups, epoxide groups and in some cases also ester groupings. The only important aspect for observing the teachings according to the invention is the hydroboration of an adequate portion of the ethylenic double bonds so that the organo boron radicals with aerobic initiator activity are formed to an adequate degree in the polymer matrix.

The polymer material may have been prepared by polymerization or copolymerization of olefinically unsaturated components, using polycondensation or polyaddition, the selection of the monomer types from which the polymers are built up guarantees the desired content of active double bonds in the polymer material for the subsequent hydroboration. Especially suitable as a polymer matrix may be unsaturated oligomers or polymers that have been prepared by polycondensation. All known polycondensate types such as polyesters, polyamides, polyimides, polycarbonates, polyurethanes and similar substances can be considered for this purpose. But oligomers or polymer types that were obtained by polyaddition are also suitable.

The oligomers or polymers are prepared preferably by the following methods: (a) By polymerization of one or several dienes or by copolymerization of such dienes with α-olefins. (b) By polymerization of diolefins that contain different active olefinic groups in the molecule, or by copolymerization of such diolefins with α-olefins. (c) By polymerization of cross-linking agents (olefinically poly-unsaturated monomers) or by copolymerization of such cross-linking agents with α-olefins. (d) By polyaddition of cyclic ethers or imines containing olefinic groups. (e) By polycondensation of dicarboxylic acids with diols or diamines containting olefin groups. (f) By polycondensation of dicarboxylic acids with diols or diamines containing olefin groups.

The polymerization, polyaddition or polycondensation can be performed with or without regulation of the molecular weight. The formed products are slightly viscous to solid, depending on the chosen monomer combination and/or by regulating condensation. The general expertise of polymer chemistry applies here for the specific case. A list of monomer reactants that can be used, for the preparation of the oligomers or polymers containing olefinic groups or used as adjuncts, follows without limiting the invention to the specifically mentioned components.

α-olefins

Unsubstituted straight-chain and/or branched alpha-olefins with 2 to 25 C-atoms, especially with 2 to 10 C atoms, vinyl derivatives such as vinyl esters, for example acetate, vinyl stearate, vinyl benzoate, but also substituted compounds such as vinyl-2-ethyl hexoate, vinyl dichloroacetate, vinyl cyanoacetate, vinyl β-butoxypropionate, α-methyl vinyl acetate and similar substances, vinyl ethers, for example vinyl methyl ether, vinyl isobutyl ether, vinyl-n-butyl ether, vinyl cyclohexyl ether, N-vinyl-substituted compounds, for example, vinyl pyrrole, vinyl carbazole, vinyl indole, vinyl imidazole vinyl diphenylamine, vinylphenyl-α-naphthylamine and others; N-vinylic acid amines, N-vinyl acid imides or N-vinyl lactams, for example vinylcaprolactam, vinyl-3-methylpyrrolidone, vinyl-N-acetylaniline, vinyl succinimide, vinyl-α imide, vinyl methylacetamide; vinyl pyridine compounds, for example 2-methyl-vinyl-pyridine, 3-methyl vinyl pyridine or 4-methylvinyl-pyridine, 5-ethyl-2-vinyl-pyridine and others; S-vinyl compounds, especially vinyl-substituted sulfides, vinyl thio esters, vinyl sulfoxides and vinyl sulfines, vinyl halides, for example vinyl chloride, acryl compounds such as acrolein, acrylic acid, (meth)acrylic acid derivatives, especially esters or amides of (meth)acrylic acid and acrylonitrile.

Dienes

Suitable monomers are, for example, 1,3-butadiene, isoprene, cyclopentadiene, chloroprene, 1,3-pentadiene, 2,3-dimethylbutadiene, 1,3-hexadiene or 2,4-hexadiene.

Diolefins

Diallyl compounds for example diallyl sulfide, diallyl phthalate, or diallyl isocyanurate, unsaturated esters of unsaturated monocarboxylic acids and diols or unsaturated amides of unsaturated carboxylic acids and diamines. Examples of unsaturated carboxylic acids are, e.g., acrylic acid, methacrylic acid, crotonic acid or undecylenic acid.

Cyclic Ethers Carrying Olefinic Groups

Suitable are, for example, vinyl-substituted epoxides or correspondingly substituted cyclic ethers with more than 2 vicinal carbon atoms in the ring, glycidyl esters of unsaturated acids such as tetrahydrophthalic acid, diglycidyl ester, or compounds such as vinylcyclohexene epoxide. The polymerization or polyaddition is started by cationically initiated reaction, for example, with boron trifluoride or its complex compounds with the simultaneous opening of the ether ring. The resulting oligomers or polymers contain the olefinic compounds for the subsequent reaction with boranes. The iodine number in the oligomer or polymer can be regulated in a well-known manner by copolymerization with cyclic ethers or cyclic imines that lack functionally active olefin groups in the molecule.

Unsaturated Dicarboxylic Acids

Dicarboxylic acid, maleic acid, fumaric acid, mesaconic acid, citraconic acid, sorbic acid, alkenylsuccinic acid and alkenylsuccinic anhydrides, alkarylsuccinic anhydrides, for example n-octadecenyl-succinic anhydride, n-octadecenyl-8-succinic anhydride.

Unsaturated Diols 2,5Dimethyl-3-hexene-2,5-diol, 2-butene-1,4-diol as well as diols that have an olefinically unsaturated functional group in a side-chain substituent. The situation is analogous for unsaturated diamines.

Suitable as saturated dicarboxylic acids diols or diamines are all known compounds of the mentioned type, for example oxalic acid, malonic acid, succinic acid, azelaic acid, sebacic acid, phthalic acid, hexahydrophthalic acid, terephthalic acid, 2,3-pyridine dicarboxylic acid, 2,3-quinoline dicarboxylic acid, diphenyldicarboxylic acid and similar compounds. Examples of saturated diols are ethylene glycol, diethylene glycol, triethylene glycol, tetraethylene glycol, propylene glycol, dipropylene glycol, 1,3-butylene glycol, 1,4-butylene glycol, 1,4-cyclohexanedime thanol, 2-methyl-1,4-butanediol, 1,6-hexanediol, 1,10-decanediol and others. Suitable diamines are for example, ethylenediamine, diethylenetriamine, triethylenetetramine, 1,2-propylenediamine, 1,3-propylenediamine, hexamethylenediamine, 1,5-diaminopentane, 1,8-diaminooctane, diaminotoluene, 4,4'diaminodiphenyl methane and comparable diamines.

The requirement of stability in atmospheric oxygen at least under normal pressure applies to all oligomers or polymers used within the scope of the invention. They are frequently built up mainly of chains or chain segments with C—C bonds, although this is by no means a prerequisite. Polyformals, for example, are known stable types of polymers with alternating—C—O bonds, which can be modified by suitable means, e.g. with side-chain substituents, in which ethylenic double bonds are present for subsequent hydroboration.

The extent of hydroboration of the polymer matrix can be decided at will within the limits of the total number of double bonds present. However, the conversion of at least a substantial part of these double bonds by introduction of the boron containing substituents has proved advantageous. In the preferred examples of the invention, for example, at least 30% and preferably at least 50% of the ethylenic double bonds originally present in the polymer matrix are hydroborated. Particularly suitable are those organic polymers in which at least 80%, preferably at least 90% or even at least 95%, of the ethylenic double bonds were reacted with the boron containing components. A practically completely hydroborated material frequently is the preferred initiator in accordance with the teachings of the invention.

Besides diborane $(BH_3)_2$ organic borane compounds with one or two organic radicals, especially hydrocarbon radicals, are suitable for the hydroboration. Here, preferred organic radicals are alkyl, cycloalkyl and/or aryl radicals, in which two radicals that may be present can be closed into a ring, with the inclusion of the boron atom. The substituent hydrocarbon radicals are limited to 25 carbon atoms or less each. Each of these radicals preferably has not more than about 12 to 15 carbon atoms.

A particularly suitable class of organic boron compounds for the preparation of the polymerization initiator component are organo-boron monohydride compounds, especially dialkylmonohydrides. Typical representatives of such boron compounds are, e.g. 9-borabicyclo(3,3,1)-nonane, diisopinocampheyl borane, dicyclohexyl borane, thexyl boran-(2,3-dimethyl-2-butyl borane), 3,5-dimethyl borinane, diisoamyl borane. The first mentioned of these compounds, 9-borabicyclo(3,3,1)-nonane, can be preferred for practical reasons. The compounds mentioned above may be prepared, for example, from sodium boron hydride and boron trifluoride with suitable olefins or diolefins. Diborane, its ether, amine or sulfide complexes may be used also for their preparation. The general rule applies that the organic boron compounds which have adequate thermal stability at room temperature and are quite resistant to the effect of atmospheric oxygen are preferred for the hydroboration of the polymer matrix.

A compilation of the possible methods for the preparation of suitable boron compounds is found in the monograph by Herbert C. Brown, "Organic Synthesis via Boranes", 1975, John Wiley & Sons, New York.

For the hydroboration, the unsaturated oligomers or polymers are converted by reaction with the chosen boron hydride compounds, preferably in solvents, with the complete exclusion of oxygen. The known solvents for organic boron compounds are especially tetrahydrofuran or polyethers such as diethylene glycol dimethyl ether, but also esters, hydrocarbon halides and similar substances, are suitable for this purpose.

The oligomeric or polymeric boron polymerization initiators according to the invention can then be isolated by distilling off the solvent. Depending on the monomer composition and the molecular weight, they are viscous to solid. They are best stored in closed containers, preferably under inert gas, for example nitrogen. These polymeric or oligomeric boroalkyl hardeners themselves are relatively stable in air. Selected polymerization initiators may be left standing, for example, in an open dish, exposed to the air and still retain an activity for the hardening of the olefinic components that is practically identical to that of the freshly prepared component or one stored away from oxygen.

The hardening of the reaction masses according to the invention is carried out by using about 0.1 to 40 percent by weight, expecially about 0.1 to 30 percent by weight of the described polymeric boron initiators calculated with regard to the portion to be polymerized. The polymeric hardeners are used preferably in amounts of about 0.5 to 10 percent by weight, calculated with regard to the portion to be polymerized.

The numerous, known compounds with polymerizable ethylenic double bonds that are normally used, for example, in cast resins, fillers and especially in reaction adhesives can be utilized as polymerizable components in the plastic masses according to the invention. Thus, the esters of acrylic acid and/or α-substituted acrylic acid such as methacrylic acid referred to as (meth)acrylic acid compounds in the following text with monovalent or polyvalent, especially divalent alcohols, are especially suitable. But other known derivatives of (meth)acrylic acid, especially the respective acid amides, which may also be substituted with hydrocarbon radicals, for example, at the amide nitrogen, are suitable as well. Other possible substituents in α-position of the acrylic acid derivatives are, for example, halogens, especially chlorine and/or bromine, cyanogen or generally alkyl radicals with up to 10 C-atoms.

To be mentioned as examples of (meth)acrylic acid esters of monovalent alcohols are: methyl(meth)acrylate, ethyl(meth)acrylate, butyl(meth)-acrylate, ethylhexyl(meth)acrylate.

Examples of respective esters with polyvalent alcohols are those with ethylene glycol, diethylene glycol, polyethylene glycol and trimethylol propane, di- and mono-(meth)acylates of glycerin, di(meth)acrylates of tri and tetraethylene glycol, of di-tri-, tetra- and pentapropylene glycol, the di-(meth)acrylates of ethoxylated of ethoxylated or propoylated diphenylol propane. Also acceptable are (meth)acrylates of alcohols that are derived from dihydroxymethyl tricyclodecane or also those that were prepared on a base of tricyclodecane, in which case two alcoholic radicals in the ring systems are extended by reaction with dicarboxylic acids such as maleic acid or also cyclohexane dicarboxylic acid or terephthalic acid.

Also useable are reaction products of the diglycidyl ether of diphenylol propane with methacrylic acid and/or acrylic acid. Reaction products of diiocyanates or triisocyanates, for example toluylene diisocyanate, diphenylmethane diisocyanate, isophoron diisocyanate trimerized toluylene isocyanate and similar compounds with hydroxyalkyl(meth)acrylates are also suitable as polymerizable components.

But polymerizable monomers such as vinyl acetate, vinyl halides, for example vinyl chloride, vinyl bromide or vinyl fluoride, styrene, divinylbenzene, crotonic and maleic acid esters or the so-called unsaturated polyester resins, which may be styrenized, in some cases, are also suitable. These last mentioned compounds generally are used only in small quantities in reaction adhesives, for example in amounts of up to 25 percent by weight of the polymerizable components.

Besides these, 2-acryloyl oxyethyl phosphate, 2-methacryloyoxy-ethyl phosphate, bis-2-acryloyloxyethylphosphate, bis-2-methacryloyloxyethyl phosphate, tris-2-acryloyloxyethyl phosphate, tris-2-methacryloyloxyethyl phosphate and acid amides such as dimethylene bis(meth)acrylamide, tetramethylene bis(meth)acrylamide, trimethylexamethylene bis(meth)acrylamide, tri(meth)acryloyl diethylenetriamine and many other similar substances are suitable.

Frequently the polymerizable masses contain preprepared polymer products such as polymethyl(meth)acrylate, copolymers of methyl(meth)acrylate, polychloroprene, chlorosulfonated polyethylene, nitrilo rubbers and urethanes for reinforcement or elastification and simultaneously as thickeners in addition to the polymerizable components. This makes the processing of the masses, for example the adhesive, easier. The know-how of the present state of the art may be applied in individual cases.

The addition of other agents such as fillers, for example quartz powder or similar substances, is advantageous or necessary in many cases. Finally, dyeing with suitable dyes or pigments can be advantageous.

The aerobically hardenable plastic materials according to the invention generally are in the form of multicomponent systems, one component consisting of the polymerizable constituent of ethylenically unsaturated monomers, and when suitable in combination with polymer fillers, dyes and similar compounds, while a separate, second component contains the organo-boron polymers. This initiator component may consist exclusively of the hydroborated polymer matrix, but there is also the possibility of using this starter diluted with solvents. Especially non-hydroborated polymers and/or also inert solvents or thinners can be considered as solvents. The absence of liquid solvents, or the presence of only limited quantities, is preferred to make the hardener component stable in contact with air.

Consequently the invention concerns particularly two-component reaction adhesives that contain, in addition to a known component which forms the adhesive substance, the organic boron oligomers or polymers of the described type as separately stored hardeners. These two-component reaction batches can be processed in a known manner, for example by mixing hardener and polymerizable reaction batch before the application of the adhesive to the material to be bonded. But the batches according to the invention are also suitable for use in the so-called no-mix adhesive systems.

The new adhesives are characterized by a fast hardening rate at room temperature and good strengths after a short time on a large number of different surfaces. Particularly noteworthy is the fact that a fast and good adhesion is obtained even on moist surfaces. The adhesives thus can be used as so-called construction adhesives for the bonding of metals, wood, glass, ceramics and plastics.

EXAMPLES (A) Preparation of the Oligomeric or Polymeric Olefins

General Instructions for the Preparation of Polymerization Products

A three-neck refined steel autoclave with stirrer, thermometer and distillation bridge was charged with acrylate, solvent (tetrahydrofuran=THF), radical starter (azoisobutyric acid nitrile=AIBN) and regulator (thiophenol) and closed. The autoclave was flushed three times with nitrogen (5 atm), and 1,3 butadiene was then added through a valved cylinder. The polymerization was carried out at 60±1° C. with agitation, over a period of 7 hours. The maximal pressure was 9 atm. The batch was removed from the autoclave and the solvent as well as unreacted monomer were separated in a rotary evaporator. The compositions of the batches and the polymer properties are found in Table A (A 1–A 4).

General Instructions for the Preparation of Polycondensates Polyesters

Alkenylsuccinic anhydride (ASA) and diol were placed in a three-neck flask with stirrer, thermometer and distillation bridge. Under nitrogen the temperature was quickly raised to 150° C. and then from 150° C. to 200° C. within 3 hours. The largest part of the water of reaction, which indicates the progress of the ester condensation, was separated during this time. The batch was allowed to cool to approx. 150° C., a vacuum of 10 torr was cautiously applied and the conversion completed at 200° C. and 10 torr. The product was drained off while hot. The composition of the batches and the polymer properties are found in Table A (A 6–10).

Polyamides

The amine was placed in a three-neck flask with stirrer, thermometer and distillation bridge, and the alkenylsuccinic anhydride (ASA) was added quickly with water cooling, while the reaction temperature was maintained at about 100° C. to keep the ammonium salt liquid. Under nitrogen, the ammonium salt was heated slowly to 200° C. during a period of 2 hours. The largest part of the water of reaction, which indicates the formation of amide, separated during this time. The batch was allowed to cool to approx. 150° C., a vacuum of 10 torr was cautiously applied and the amide formation was completed at 200° C. and 10 torr. The product was drained off while hot. The composition of the batches and the oligomer or polymer properties are found in Table A (A 11–A 15).

TABLE A

Summary of the prepared oligomeric and polymeric olefins/polymerization products

| | Polymerization batch | | | | | Results | | | |
|---|---|---|---|---|---|---|---|---|---|
| | Amounts of monomer | | AIBN | Thiophenol | THF | Mol % Butadiene | | Properties | Conversion |
| No. | used | g | g | g | g | in monomer mixture | in polymer[1] | of polymer | % |
| A1 | butadiene 21.6 | methyl acrylate 137.8 | 1.6 | 0.92 | 35 | 20 | 38 | highly viscous oil | 20 |
| A2 | butadiene | methyl | 8.0 | 11.60 | 1400 | 20 | 44 | viscous | 17 |

TABLE A-continued
Summary of the prepared oligomeric and polymeric olefins/polymerization products

| No. | | | | | | | | | |
|---|---|---|---|---|---|---|---|---|---|
| | 108 | acrylate 689 | | | | | | oil | |
| A3 | butadiene 270 | butyl acrylate 641 | 8.0 | 11.60 | 1700 | 50 | 7.2 | highly viscous oil | 73 |
| A4 | butadiene 54 | butyl acrylate 513 | 4.0 | — | 1700 | 20 | 4.2 | very highly viscous oil | 85 |

| | Polymerization batch | | Results | | | |
|---|---|---|---|---|---|---|
| No. | Amount of educt used per gram | | Properties of polymer | Acid No. | Iodine No. | Mols double bonding/100 g oligomer/polymer |
| A6 | iso $C_8$—ASA 63.3 | hexamethylene glycol 35.4 | viscous, brownish | 48 | 77.7 | 0.32 |
| A7 | $C_{10}$—ASA 239 | hexamethylene glycol 118 | viscous, light yellow | 27 | 72.9 | 0.29 |
| A8 | $C_{16}$—ASA 323 | hexamethylene glycol 118 | slightly viscous brownish | 42 | 55.0 | 0.24 |
| A9 | maleic acid 232.16 | hexamethylene glycol 236 | solid, white | 0 | 128 | 0.5 |
| A10 | maleic acid 58.05 adipic acid 292.3 | hexamethylene glycol 292 | solid, white | 4.2 | 20 | 0.08 |

| | Polymerization batch | | Results | | | |
|---|---|---|---|---|---|---|
| No. | Amount of educt used per gram | | Properties of polymer | Amine No. | Iodine No. | Mols double-bonding/100 g oligomer/polymer |
| A11 | iso $C_8$ ASA 58.5 | trimethylhexa-methylenediamine 43.8 | viscous, brown | 115 | 69.3 | 0.29 |
| A12 | $C_{10}$ ASA 239 | trimethylhexa-methylenediamine 158 | low viscosity, light brown | 115 | 76.2 | 0.26 |
| A13 | $C_{10}$ ASA 169.7 | trimethylhexa-methylenediamine 75.4 | viscous, light brown | 29 | 78.3 | 0.35 |
| A14 | $C_{16}$ ASA 286 | trimethylhexa-methylenediamine 139.9 | low viscosity, brown-green | 98 | 60.7 | 0.22 |
| A15 | $C_{16}$ ASA 195 | trimethylhexa-methylenediamine 67.2 | viscous, brown green | 31 | 58.3 | 0.29 |

[1]Determined by $^1$H-NMR
ASA = alkenylsuccinic anhydride

(B) Preparation of the Oligomeric or Polymeric Boroalkyl Starters

For the removal of the residual oxygen, the oligoolefins or polyolefins were dissolved in an equal amount of degassed THF and the solvent was removed under a vacuum of $10^{-4}$ torr. In a glovebox, equal parts by weight of freshly distilled, degassed THF were again added, and the oligomeric or polymeric olefins were dissolved. With complete protection against oxygen, the amounts of 9-borabicyclo(3,3,1)nonane (9-BBN) listed in Table B were added, and the mixture was agitated until the 9-BBN was quantitatively dissolved. Then, the solution was heated at 60° C. for one hour with agitation. The THF was distilled under vacuum and the storage container was closed. Samples are removed under protective gas and with complete protection against oxygen. (See Table B)

TABLE B
Summary of the prepared oligomeric and polymeric boralkyls

| No. | Olefin used g | 9-BBN g | Degree of modification at the double bond % | Properties |
|---|---|---|---|---|
| B1 | A1/10 | 1.0 | 22 | highly viscous |
| B2 | A2/10 | 1.0 | 18 | viscous |
| B3 | A3/10 | 0.72 | 100 | highly viscous |
| B4 | A4/10 | 0.4 | 100 | thick, viscous |
| B5 | poly-(cis-1,4-butadien-1,3)[1]/10 | 0.7 | 3 | viscous |
| B6 | A6/50 | 19.5 | 100 | homogeneous, tough, orange |
| B7 | A7/50 | 17. | 100 | homogeneous, highly viscous, light yellow |
| B8 | A8/50 | 14.6 | 100 | homogeneous, highly viscous light yellow |
| B9 | A9/50 | 15.4 | 50 | homogeneous, highly viscous |

TABLE B-continued

Summary of the prepared oligomeric and polymeric boralkyls

| No. | Olefin used g | 9-BBN g | Degree of modification at the double bond % | Properties |
|---|---|---|---|---|
| B10 | A10/50 | 4.8 | 100 | red-brown powder, light yellow |
| B11 | A11/50 | 17.7 | 100 | homogeneous, solid, orange |
| B12 | A12/50 | 15.8 | 100 | homogeneous, solid, light yellow |
| B13 | A13/50 | 21.4 | 100 | homogeneous, solid, orange |
| B14 | A14/50 | 13.5 | 100 | homogeneous, tough, yellow |
| B15 | A15/50 | 17.7 | 100 | homogeneous, viscous, yellow-orange |

[1]Polyol 130 by CWH, Huls (c) Use of the Oligomeric or Polymeric Boroalkyls as Hardeners for Monomer (Adhesives)

General Instructions

In a glass beaker, 40 g polymethacrylic acid methyl ester (PMMA, commercial powder "Plexigum MB 319" by Röhm, Darmstadt) were dissolved in 45 g methyl methacrylate (MMA) and 5 g methacrylic acid (MAA) with stirring. Between 1.5 and 23 percent by weight of the oligomeric or polymeric boroalkyl initiators described under B (cf. Table C 1–C 15) were added to 5 gram samples of the above mixture with continued vigorous agitation. The pot lives of the mixtures vary between 1 and 13 minutes. These adhesives were used to glue sandblasted and degreased sheets of iron together during the pot life, and after 24 hours, strengths were measured in the tensile and shear test according to DIN 53 381/3. The results are compiled in Tables 1–5.

The high stability of the prepared boroalkyl oligomers or polymers in atmospheric oxygen was determined in another test series by storing them in the open container exposed to air for between 24 and 72 hours and using and testing them subsequently as hardeners. The pot lives and tensile and shear strengths are given in parentheses in Tables C 1–C 15.

Table C 1

Pot lives and tensile and shear strengths on sandblasted and degreased sheet iron test pieces, using the boroalkyl oligomer from Example B 1 to harden methacrylate adhesives (40 g PMMA, 45 MMA, 5 g MAA).

| Hardener concentration % by wt. | Pot life min. | Tensile and shear strength $\frac{N}{mm^2}$ |
|---|---|---|
| 1.5 | 10 | 19 |
| 3 | 10 | 20 |
| 5 | 5 | 24 |
| 10 | 5 | 12 |
| 23 | 2 | 9 |

Table C 2

Pot lives and tensile and shear strengths on standblasted and degreased sheet iron test pieces, using the boroalkyl oligomer from Example B 2 as hardener for methacrylate adhesives (40 g PMMA, 45 g MMA, 5 g MAA).

| Hardener concentration % by wt. | Pot life min. | Tensile and shear strength $\frac{N}{mm^2}$ |
|---|---|---|
| 1.5 | 10 (12) | 21 (10) |
| 3 | 5 (7) | 25 (24) |
| 5 | 5 (5) | 29 (30) |
| 10 | 5 (5) | 27 (28) |
| 23 | 5 (4) | 13 (24) |

The figures in parentheses indicate the measured data obtained when the boroalkyl hardener was stored exposed to air for 24 hours, at room temperature, before its use.

Table C 3

Pot lives, tensile and shear strengths on sandblasted and degreased sheet iron test pieces, using the boroalkyl oligomer from Example B 3 as hardener for methacrylate adhesives (40 g PMMA, 45 g MMA, 5 g MAA).

| Hardener concentration % by wt. | Pot life min. | Tensile and shear strength $\frac{N}{mm^2}$ |
|---|---|---|
| 1.5 | 8 (11) | 16 (5) |
| 3 | 9 (8) | 27 (14) |
| 5 | 4 (5) | 29 (28) |
| 10 | 3 (4) | 28 (27) |
| 23 | 3 (3) | 26 (24) |

The figures in parentheses indicate the measured data obtained when the boroalkyl hardener was stored exposed to air, at room temperature, 72 hours before its use.

Table C 4

Pot lives, tensile and shear strengths on sandblasted and degreased sheet iron test pieces, using the boroalkyl polymer from Example B 4 as hardener for methacrylate adhesives (40 g PMMA, 45 g MMA, 5 g MAA).

| Hardener concentration % by wt. | Pot life min. | Tensile and shear strength $\frac{N}{mm^2}$ |
|---|---|---|
| 1.5 | 4 (11) | 0 (0) |
| 3 | 2.5 (11) | 16 (0.4) |
| 5 | 2 (9) | 15 (0.8) |
| 10 | 1.5 (3) | 19 (3.5) |
| 23 | 1.5 (2) | 9 (13) |

The figures in parentheses indicate the data measured when the boroalkyl hardener was stored exposed to air, at room temperature, 24 hours before its use.

Table C 5

Pot lives and tensile and shear strengths on sandblasted and degreased sheet iron tests pieces, using the boroalkyl oligomer from Example B 5 as hardener for methacrylate adhesives (40 g PMMA, 45 g MMA, 5 g MAA).

| Hardener concentration % by wt. | Pot life min. | Tensile and shear strength $\frac{N}{mm^2}$ |
|---|---|---|
| 1.5 | 2.5 (8) | 9 (1) |
| 3 | 3 (7) | 18 (8) |
| 5 | 2 (2) | 21 (16) |
| 10 | 2 (2) | 17 (17) |
| 23 | 1 (1) | 2 (3) |

The figures in parentheses indicate the data measured when the boroalkyl hardener was stored exposed to air, at room temperature, 24 hours before its use.

Table C 6

Pot lives and tensile and shear strengths on sandblasted and degreased sheet iron test pieces, using the boroalkyl oligomer from Example B 6 as hardener for methacrylate adhesives (40 g PMMA, 45 g MMA, 5 g MMA).

| Hardener concentration % by wt. | Pot life min. | Tensile and shear strength $\frac{N}{mm^2}$ |
|---|---|---|
| 1.5 | 7 | 17 |
| 3 | 5 (6) | 26 (26) |
| 5 | 4 (4.5) | 27 (28) |
| 10 | 3 (4) | 26 (30) |
| 23 | 2.5 (3) | 20 (24) |

The figures in parentheses indicate the data measured when the boroalkyl hardener was stored at room temperature, exposed to air, 48 hours before its use.

Table C 7

Pot lives, tensile and shear strengths on sandblasted and degreased sheet iron test pieces, using the boroalkyl oligomer from Example B 7 as hardener for methacrylate adhesives (40 g PMMA, 45 MMA, 5 g MMA).

| Hardener concentration % by wt. | Pot life min. | Tensile and shear strength $\frac{N}{mm^2}$ |
|---|---|---|
| 1.5 | 6 | 9 |
| 3 | 5 (6) | 23 (21) |
| 5 | 4 (5) | 25 (27) |
| 10 | 4 (4) | 22 (23) |
| 23 | 2.5 (0.5) | 15 (18) |

The figures in parentheses indicate the data measured when the boroalkyl hardener was stored at room temperature, exposed to air, 24 hours before its use.

Table C 8

Pot lives, tensile and shear strengths on sandblasted and degreased sheet iron test pieces, using the boroalkyl oligomer from Example B 8 as hardener for methacrylate adhesives (40 g PMMA, 45 g MMA, 5 g MMA).

| Hardener concentration % by wt. | Pot life min. | Tensile and shear strength $\frac{N}{mm^2}$ |
|---|---|---|
| 1.5 | 8 | 12 |
| 3 | 6 (8) | 20 (16) |
| 5 | 4 (5.5) | 24 (26) |
| 10 | 3.5 (4) | 21 (24) |
| 23 | 2 (2) | 13 (16) |

The figures in parentheses indicate the data measured when the boroalkyl hardener was stored at room temperature, exposed to air 48 hours before its use.

Table C 9

Pot lives and tensile and shear strength on sandblasted and degreased sheet iron test pieces, using the boroalkyl oligomer from Example B 9 as hardener for methacrylate adhesives (40 g PMMA, 45 g MMA, 5 g MAA).

| Hardener concentration % by wt. | Pot life min. | Tensile and shear strength $\frac{N}{mm^2}$ |
|---|---|---|
| 1.5 | 12 (9) | 25 (23) |
| 3 | 12 (5.5) | 30 (27) |
| 5 | 11.5 (4.5) | 32 (29) |
| 10 | 8.5 (3.5) | 26 (29) |
| 23 | 5 (3) | 20 (27) |

The figures in parentheses indicate the data measured when the boroalkyl hardener was stored at room temperature exposed to air 24 hours before its use.

Table C 10

Pot lives, tensile and shear strengths on sandblasted and degreased sheet iron test pieces, using the boroalkyl oligomer from Example B 10 as hardener for methacrylate adhesives (40 g PMMA, 45 g MMA, 5 g MAA).

| Hardener concentration % by wt. | Pot life min. | Tensile and shear strength $\frac{N}{mm^2}$ |
|---|---|---|
| 1.5 | 7 (9.5) | 27 (3) |
| 3 | 6.5 (13.5) | 29 (11) |
| 5 | 6.5 (12) | 28 (24) |
| 10 | 6.5 (11) | 29 (21) |
| 23 | 6 (20) | 27 (1) |

The figures in parentheses indicate the data measured when the boroalkyl hardener was stored at room temperature exposed to air 24 hours before its use.

Table C 11

Pot lives, tensile and shear strengths on sandblasted and degreased sheet iron test pieces, using the boroalkyl oligomer from Example B 11 as hardener for methacrylate adhesives (40 g PMMA, 45 g MMA, 5 g MAA).

| Hardener concentration % by wt. | Pot life min. | Tensile and shear strength $\frac{N}{mm^2}$ |
| --- | --- | --- |
| 1.5 | 4 (6) | 17 (17) |
| 3 | 4 (5) | 18 (24) |
| 5 | 3 (5) | 16 (27) |
| 10 | 2 (3) | 8 (21) |
| 23 | 1.5 (2) | 4 (13) |

The figures in parentheses indicate the data measured when the boroalkyl hardener was stored at room temperature, exposed to air 24 hours before its use.

Table C 12

Pot lives, tensile and shear strengths on sandblasted and degreased sheet iron test pieces, using the boroalkyl oligomer from Example B 12 as hardener for methacrylate adhesives (40 g PMMA, 45 g MMA, 5 g MAA).

| Hardener concentration % by wt. | Pot life min. | Tensile and shear strength $\frac{N}{mm^2}$ |
| --- | --- | --- |
| 1.5 | 12 (11) | 14 (13) |
| 3 | 9 (10) | 27 (17) |
| 5 | 7 (5) | 30 (26) |
| 10 | 5 (4) | 26 (23) |
| 23 | 3 (3) | 20 (11) |

The figures in parentheses indicate the data measured when the boroalkyl hardener was stored at room temperature, exposed to air, 24 hours before its use.

Table C 13

Pot lives, tensile and shear strengths on sandblasted and degreased sheet iron test pieces, using the boroalkyl oligomer from Example B 13 as hardener for methacrylate adhesives (40 g PMMA, 45 g MMA, 5 g MAA).

| Hardener concentration % by wt. | Pot life min. | Tensile and shear strength $\frac{N}{mm^2}$ |
| --- | --- | --- |
| 1.5 | 8 (8) | 20 (20) |
| 3 | 6 (6) | 24 (25) |
| 5 | 5 (5) | 25 (28) |
| 10 | 4 (4) | 18 (20) |
| 23 | 2.5 (2.5) | 1 (12) |

The figures in parentheses indicate the data measured when the boroalkyl hardener was stored at room temperature, exposed to air 24 hours before its use.

Table C 14

Pot lives, tensile and shear strengths on sandblasted and degreased sheet iron test pieces, using the boroalkyl oligomer from Example B 14 as hardener for methacrylate adhesives (40 g PMMA, 45 g MMA, 5 MAA).

| Hardener concentration % by wt. | Pot life min. | Tensile and shear strength $\frac{N}{mm^2}$ |
| --- | --- | --- |
| 1.5 | 8 (12) | 8 (20) |
| 3 | 6 (10) | 15 (18) |
| 5 | 5 (10) | 18 (18) |
| 10 | 3.5 (4) | 17 (16) |
| 23 | 2 (3.5) | 11 (12) |

The figures in parentheses indicate the data measured when the boroalkyl hardener was stored at room temperature, exposed to air 24 hours before its use.

Table C 15

Pot lives, tensile and shear strengths on sandblasted and degreased sheet iron test pieces, using the boroalkyl oligomer from Example B 15 as hardener for methacrylate adhesives (40 g PMMA, 45 g MMA, 5 g MAA).

| Hardener concentration % by wt. | Pot life min. | Tensile and shear strength $\frac{N}{mm^2}$ |
| --- | --- | --- |
| 1.5 | 8 (8) | 21 (18) |
| 3 | 5.5 (6) | 24 (28) |
| 5 | 3.5 (4) | 19 (23) |
| 10 | 4.5 (4) | 15 (20) |
| 23 | 2.5 (3) | 3.6 (16) |

The figures in parentheses indicate the data measured when the boroalkyl hardener was stored at room temperature, exposed to air 24 hours before its use.

Aluminum and beech wood test pieces were treated in an identical manner, glued with a simple overlap and the tensile and shear strengths were determined.

Adhesives based on triethylene glycol dimethacrylate and bisphenol A-dimethacrylate (Diacryl 101, by AKZO Chem) were also polymerized with the hardeners from Examples B 2 and B 3. Sheet iron and aluminum were glued together with these with a simple overlap. The results of the tensile and shear strength tests are found in Table C 16. The test pieces stored for 24 hours at room temperature between gluing and testing.

The preceding specific embodiments are illustrative of the practice of the invention. It is to be understood, however, that other expedients known to those skilled in the art or disclosed herein, may be employed without departing from the spirit of the invention or the scope of the appended claims.

TABLE C

Tensile and shear strengths after gluing with methacrylate adhesives with the oligomeric boralkyls from Example B2 and B3

| Adhesive | | | Hardener | | Glued | Tensile and shear strength |
| --- | --- | --- | --- | --- | --- | --- |
| Monomer 1 | Monomer 2 | Polymer | No. | Conc./wt % | material | Nmm$^{-2}$ |
| methyl methacrylate 45 g | methacrylic acid 5 g | polymethyl methacrylate 40 g | B2 | 5 | aluminum | 8 |
| | | | B3 | 5 | beech wood | 3 |
| | | | | | aluminum | 14 |
| triethylene glycol dimethacrylate | methacrylic acid | polymethyl methacrylate | B2 | 3 | iron | 14 |
| | | | | | aluminum | 9 |
| | | | B3 | 3 | iron | 14 |

TABLE C-continued

Tensile and shear strengths after gluing with methacrylate adhesives with the oligomeric boralkyls from Example B2 and B3

| Adhesive | | | Hardener | | Glued | Tensile and shear strength |
|---|---|---|---|---|---|---|
| Monomer 1 | Monomer 2 | Polymer | No. | Conc./wt % | material | Nmm$^{-2}$ |
| acrylate 75 g diacryl 101 (bishenol A-dimethacrylate) 75 g | 5 g methacrylic acid 5 g | 20 g polymethyl methacrylate 20 g | B2 B3 | 3 3 | iron aluminum iron | 10 11 10 |

I claim:

1. An aerobically hardenable plastic composition comprising
   (a) a component containing polymerizable ethylenic double bonds, and
   (b) an organo-boron compound having a boron-free polymer matrix with at least one organic polymer chain to which are attached, as side chains by hydroboration of ethylenic double bonds, boron-containing groups of the structure $R_1R_2B$— in which $R_1$ is a hydrocarbon radical having up to 25 carbon atoms and $R_2$ is either hydrogen, a hydrocarbon radical having up to 25 carbon atoms, or together with $R_1$ forms a cyclic hydrocarbon radical having up to 25 carbon atoms, each end of which is bound to the boron atom with a boron-carbon bond, said boron-free polymer matrix being largely inert to atmospheric oxygen and having an iodine number of from about 1 to about 500 before hydroboration.

2. A plastic composition in accordance with claim 1, wherein the boron containing groups in the organo-boron compound in (b) are connected to the polymer matrix mainly by boron to carbon bonds.

3. A plastic composition in accordance with claim 1 wherein the polymer maxtrix in (b) has a mean molecular weight in the range of from about 150 to about 3,000,000.

4. A plastic composition in accordance with claim 1 wherein the polymer matrix in (b) has a mean molecular weight in the range of from about 300 to about 500,000.

5. A plastic composition in accordance with claim 1 wherein the polymer matrix in (b) has a mean molecular weight in the range of from about 500 to about 10,000.

6. A plastic composition in accordance with claim 1 wherein the polymer matrix in (b) has ethylenically unsaturated oligomers or polymers present and at least a portion of the double bonds are converted to saturated bonds by the introduction of boron containing groups by means of hydroboration.

7. A plastic composition in accordance with claim 6 wherein at least 30% of the ethylenic double bonds originally present in the polymer matrix in (b) are hydroborated.

8. A plastic composition in accordance with claim 6 wherein at least 50 % of the ethylenic double bonds originally present in the polymer matrix in (b) are hydroborated.

9. A plastic composition in accordance with claim 6 wherein at least 95% of the ethylenic double bonds originally present in the polymer matrix in (b) are hydroborated.

10. A plastic composition in accordance with claim 1 wherein the polymer matrix in (b) contains mainly carbon to carbon bonds in the polymer chains.

11. A plastic composition in accordance with claim 1 wherein the polymer matrix in (b) has a straight chain or branched chain structure.

12. A plastic composition in accordance with claim 1 wherein the polymer matrix in (b) is a polymerization or copolymerization product, or a polycondensate or a corresponding polyaddition product with ethylenic double bonds.

13. A plastic composition in accordance with claim 1 wherein the polymer matrix in (b) has an iodine number in the range of about 5 to about 100.

14. A plastic composition in accordance with claim 1 wherein the polymer matrix in (b) has an iodine number in the range of about 8 to about 50.

15. A plastic composition in accordance with claim 1 wherein the double bonds of the polymer matrix in (b) subjected to introduction or organo-boron bonding by hydroboration are in any or all of the organic polymer chains of the polymer matrix.

16. A plastic composition in accordance with claim 1 wherein oligomers or polymers with olefinically unsaturated double bonds prepared by diene polymerization or copolymerization of dienes with olefinically unsaturated monomers are present as the polymer matrix in (b).

17. A plastic composition in accordance with claim 1 wherein in (b) olefinically unsaturated polyesters were used as the polymer matrix having at least part of their double bonds located in side chains.

18. A plastic composition in accordance with claim 1 wherein said composition is in the form of a two-component adhesive consisting of component (b) as a starter system and component (a) which is maintained separately from component (b).

19. A plastic composition in accordance with claim 18 wherein one or both of components (a) and (b) are fluid or spreadable at room temperature.

20. A plastic composition in accordance with claims 18 or 19 wherein the polymerizable component (a) is suitable as an adhesive and is based on ester or amide derivatives of acrylic acid or α-substituted acrylic acids, which can be polymerized by radical polymerization and which contains these polymerizable components in generally homogeneous mixture.

21. A plastic composition in accordance with claim 1 wherein in (b) the hydrocarbon radicals contain up to 15 carbon atoms.

22. A plastic composition in accordance with claim 1 wherein in (b) the hydrocarbon radicals contain up to 12 carbon atoms.

23. A plastic composition according to claim 1, wherein the organo-boron compound in (b) is formed from hydroboration using an organo-boron monohydride.

24. A plastic composition according to claim 23, wherein the organo-boron monohydride is a dialkylmonohydride.

25. A plastic composition according to claim 24, wherein the dialkylmonohydride is selected from the group consisting of 9-boro-bicyclo-(3,3,1)-nonane, diisopinocampheyl borane, dicyclohexyl borane, thexylborane, 3,5-dimethylborinane, and diisoamyl borane.

26. A plastic composition in accordance with claim 1 wherein in (b) said polymer matrix before hydroboration is either (a) copolymer of an acrylic acid ester and butadiene, (b) a polyester of alkenylsuccinic acid anhydride with a diol, or (c) a polyamide of alkenylsuccinic acid anhydride with a diamine.

27. A plastic composition in accordance with claim 1 wherein said polymer matrix before hydroboration is prepared by either.

(a) polymerization of one or more dienes or by copolymerization of such diene or dienes with one or more alpha-olefins;

(b) polymerization of one or more diolefins that contain different active olefinic groups in the molecule, or by copolymerization of such diolefin or diolefins with one or more alpha-olefins;

(c) polymerization of an olefinically polyunsaturated monomer crosslinking agent or by copolymerization of such crosslinking agent with one or more alpha-olefins;

(d) polyaddition of cyclic ethers or imines containing olefinic groups;

(e) polycondensation of dicarboxylic acids containing olefin groups with diols or diamines; or (f) polycondensation of dicarboxylic acids with diols or diamines containing olefin groups.

* * * * *